(12) United States Patent
Lüth et al.

(10) Patent No.: US 6,620,614 B1
(45) Date of Patent: Sep. 16, 2003

(54) SOLID-STATE FERMENTER AND METHOD FOR SOLID-STATE FERMENTATION

(75) Inventors: Peter Lüth, Wismar (DE); Ute Eiben, Malchow (DE)

(73) Assignee: Prophyta Biologischer Pflanzenschutz GmbH, Malchow (DE)

( * ) Notice: Subject to any disclaimer, the term of this patent is extended or adjusted under 35 U.S.C. 154(b) by 0 days.

(21) Appl. No.: 09/674,372

(22) PCT Filed: Apr. 27, 1999

(86) PCT No.: PCT/DE99/01271
§ 371 (c)(1),
(2), (4) Date: Dec. 4, 2000

(87) PCT Pub. No.: WO99/57239
PCT Pub. Date: Nov. 11, 1999

(30) Foreign Application Priority Data

Apr. 30, 1998 (DE) .......................................... 198 20 169

(51) Int. Cl.⁷ ................................................ C12C 1/15
(52) U.S. Cl. .............................. 435/291.3; 435/291.6; 435/293.2; 435/294.1; 435/813; 435/819
(58) Field of Search ........................ 435/286.7, 289.1, 435/291.1, 291.3, 291.6, 293.2, 294.1, 813, 819

(56) References Cited

U.S. PATENT DOCUMENTS 5,595,910 A * 1/1997 Kant et al. .................. 210/617
6,197,573 B1 * 3/2001 Suryanarayan et al. .. 435/286.7

FOREIGN PATENT DOCUMENTS

| DE | 44 06 632 | 10/1995 | ............ C12M/3/00 |
| EP | 0 683 815 | 2/1994 | ............ C12M/1/16 |
| FR | 2 583 059 | 6/1985 | ............ C12N/1/14 |

OTHER PUBLICATIONS

M. Ramana Murthy et al.; "Biochemical Engineering Aspects of Solid–state Fermentation" Advances in Applied Microbiology, vol. 38, 1993, pp. 99–147.
D. Bahr et al.; Solid–state Fermentation von Starterkulturen in der Gas–Feststoff–Wirbelschicht BIO forum 1; Feb. 1995; pp. 16–21.
G. Saucedo–Castaneda, et al.; "Heat Transfer Simulation in Solid Substrate Fermentation" Biotechnology and Bioengineering, vol. 35, 1990; pp. 802–808.

* cited by examiner

Primary Examiner—David A. Redding
(74) Attorney, Agent, or Firm—Norris McLaughlin & Marcus

(57) ABSTRACT

The invention concerns a solid state fermenter in particular for large volumes as well as a procedure for solid state fermentation.

The task of the present invention was the development of a solid state fermenter for large volumes and of a procedure for solid state fermentation, that allows an economic application of the solid state fermentation for little competitive micro-organisms in large fermenters.

The solid state fermenter according to the invention is characterized by representing a module fermenter, where at least two module bases, that are permeable for air and water, are arranged on top of each other, which are connected with the wall of the vessel in such a manner, that neither air nor water can pass laterally, the existence of a cultivation substrate for the micro-organisms, which have to be cultivated, on the module bases, a cooling device below every module base and the fermenter being closed with a lid.

14 Claims, 4 Drawing Sheets

SOLID-STATE FERMENTER AND METHOD FOR SOLID-STATE FERMENTATION

BACKGROUND OF THE INVENTION

The invention concerns a solid-state fermenter in particular for high volumes as well as a procedure for solid-state fermentation.

STATE OF THE ART

The submerged or solid-state fermentation is used for the mass cultivation of microorganisms with the goal of either isolating the microorganisms themselves or the metabolic product or a microbial altered substrate (e.g. in the food-processing industry). Whereas nowadays submerged fermenters (fermenters with a liquid nutritive substrate) already are built with a capacity of up to 200.000 liters, it has still not yet been achieved to build solid state fermenters (fermenter with a solid nutritive substrate) with economically relevant volumes, that can be kept free of contaminations by foreign micro-organisms for longer periods and that allow an optimum in cultivation care at the same time. However, certain filamentous fungi need surface structures, which allow them to develop and sporulate there. The largest fermenter for the production of filamentous fungi, which avoids any foreign contamination is located in the INRA in France (Durand 1997, verbal communication) and has a capacity of 50 liters. However, the capacity of this fermenter is not at all sufficient for an economic production of fungal spores that can be used, e.g., as biological agricultural pesticides.

The solid-state fermentation (SSF) is defined as growth of microorganisms—usually fungi—on solid substrates in a defined gas phase, but without a free water phase. SSF was already used for the production of fermented food, of enzyme products (Koji) or of edible mushrooms in certain territories of the Orient, Asia and Africa in the Ancient World. The efforts in the Western countries were focused on the submerged fermentation since 1940; whereas the SSF was only used for a reprocessing of organic waste. However, many institutes and firms recently show their interest in the SSF, because there are certain advantages compared to the submerged fermentation. Such advantages compared to the submerged fermentation are:

- Possibility of an effective production of secondary metabolites such as enzymes, aroma substances, aromatic substances and coloring substances as well as pharmaceutically active substances
- Possibility of a production of microorganisms as biological agents in agricultural pesticides
- Elimination of toxins or other detrimental substances from food and feeding stuff or enrichment of proteins or vitamins this stuff.

Fundamentally, there are 6 types of solid-state fermenters:

1. tray bioreactor
2. packed bed bioreactor
3. rotary drum bioreactor
4. swing solid state bioreactor
5. stirred vessel bioreactor
6. air solid fluidized bed bioreactor The first type—the tray bioreactor—, where the substrate to be fermented is spread out flatly in a container especially intended for this purpose and that is incubated in a room, which is especially air-conditioned for this reason ('Koji'—Raum, Ramana Murthy, M. V.; Karanth, N. G.; Raghava Rao, K. S. M. S.: Advance in Applied Microbiology 38 (1993), 99–147), can be used for the production of large amounts of the product, however, it has to be possible to neglect a small contamination by nucleus of crystallization by this method. Moreover, reactor and method are very space- and labor-intensive. The fermented substrate has to be moved manually within the containers. It is not appropriate for the production of large amounts of fungal spores of little competitive species.

In the 'packed bed bioreactor' a moist granular substrate, which is located in a closed container, is inoculated with a micro-organism, which develops in there without the substrate being moved. For that purpose, the substrate has to be perfused constantly by air. The following problems occur, that do not allow the use of large amounts of substrate from the beginning.

1. The micro-organism produces heat (300 kJ per kg dry weight and hour, Saucedo-Castaneda, G.; Gutierrez-Rojas, M.; Bacquet, G.; Raimbault, M.; Viniegra-Gonzalez, G.: Biotechnologie and Bioengeniering 35 (1990), 802–808), which can either be evacuated through the outer wall of the container or through an increased air-circulation (evaporation coldness). This is not possible, if the containers have large volumes. The micro-organisms slow down their growth with an increase in heat evolution and finally necrotize.
2. A constant aeration dries the substrate out. Thus, the 'loss' caused by this, creates air-channels. Their existence cannot guarantee an even aeration of the substrate any longer. The gradual drying out of the substrate also leads to deterioration in growth of the micro-organism.

The 'rotary drum bioreactor' consists of a cylindrical container, which is allocated horizontally and pivoted. The container is filled up to no more than one third of its volume with a granular cultivation substrate, where the micro-organism grows. The heat generated by the growth of the micro-organism can be evaporated to a large extent by the partially cooled shell of the container. This happens during the cylinder's slow rotation, which leads to the result, that the substrate comes again and again into contact with the shell and that it can evolve heat to it. However, the method has the disadvantage, that shear forces have an effect within the moving substrate, which lead especially to a destruction of fungal structures in development (mycelium, sporangium, fructovegetative body). In this way, it is, for example, for many fungi from the beginning not possible to obtain the goal of a high yield in spores. The problem of exsiccation is solved in this type of fermenter to a large extent by an aeration with moist air, because it is not necessary to evaporate the water from the substrate (evaporation coldness is not necessary). Moreover, spray nozzles, could achieve a moistening of the substrate, too providing a good distribution of free water by means of the movement.

However, large amounts of cultivation substrate lead to other problems in this type of fermenter:

1. The design of large fermenters is very costly.
2. The continuous movement of the fermenter can bring about an agglomeration of the moist substrate.
3. Interfaces to the exterior are necessary (air inlet and air outlet, water supply), which could easily become sources of foreign contamination by the rotation of the fermenter.

A similar fermenter as the 'rotary drum bioreactor' is the 'swing solid state bioreactor', with the only difference that the mixing of the substrate is not caused by rotary movement here, but by a shaking movement. Otherwise, the same, already mentioned advantages and disadvantages apply. An additional limitation of the volume for this type of fermenter is, however, applies, because the construction of the complicated shaking mechanism would hardly allow a weight of more than 100 kg for the filled container.

The 'stirred vessel bioreactor' can be described as a closed tank with a stirrer moving within. The problems for the use of large amounts of substrate are inevitable for this type of reactor, as these amounts can no longer be moved evenly without causing destructions in the structure of the substrates.

The cultivation substrate for the micro-organisms is kept constantly in a fluidized bed in the 'air solid fluidized bed bioreactor', which makes a relatively large volume of the reactor room necessary. The necessary air for keeping the fluidized bed up is conducted in a circulation. The air must be kept with an exactly calculated moisture content. This procedure requires a lot of energy for keeping the fluidized bed up. It could be demonstrated in an AiF project already conducted (Bahr, d.; Menner, M.: BIOforum 18 (1995), 16–21), that the cultivation of yeast cells is possible in the fluidized bed.

However, this was only achieved on a relatively small scale and at with rather small yields in comparison to the submerged fermentation. A cultivation of filamentous fungi on large amounts of granular cultivation substrate (more than 100 kg per batch) over several weeks with this technique is only possible at high costs, which are out of court.

Other state-of-the-art fermenters are too small to gain with them an economically profitable amount of fungal spores (EP-A1-0 683 815 and FR 85.08555), or it is not possible to exclude for a sufficient fermenter capacity a contamination of the cultivation substrate with nucleus of crystallization over a longer period of time (DE 4406632 C1).

SUMMARY OF THE INVENTION

Thus, the task for the present invention was to develop a SSF fermenter for large volumes and to provide a procedure for solid-state fermentation, which allows an economic application of the SSF of little competitive microorganisms in large fermenters.

It has to:
1. avoid a foreign contamination of the fermenter (keeping up of sterile conditions during the entire process of fermentation),
2. evacuate the heat, which is caused by the fungal metabolism without an exsiccation of the substrate (by increased air flow and use of the evaporation coldness),
3. avoid the occurrence of shear forces in the fermenter (no movement of the cultivation substrate) and
4. guarantee an even aeration (avoiding the exsiccation) and control over the temperature of the substrate.

DESCRIPTION OF THE PREFERRED EMBODIMENT

Figure 1:
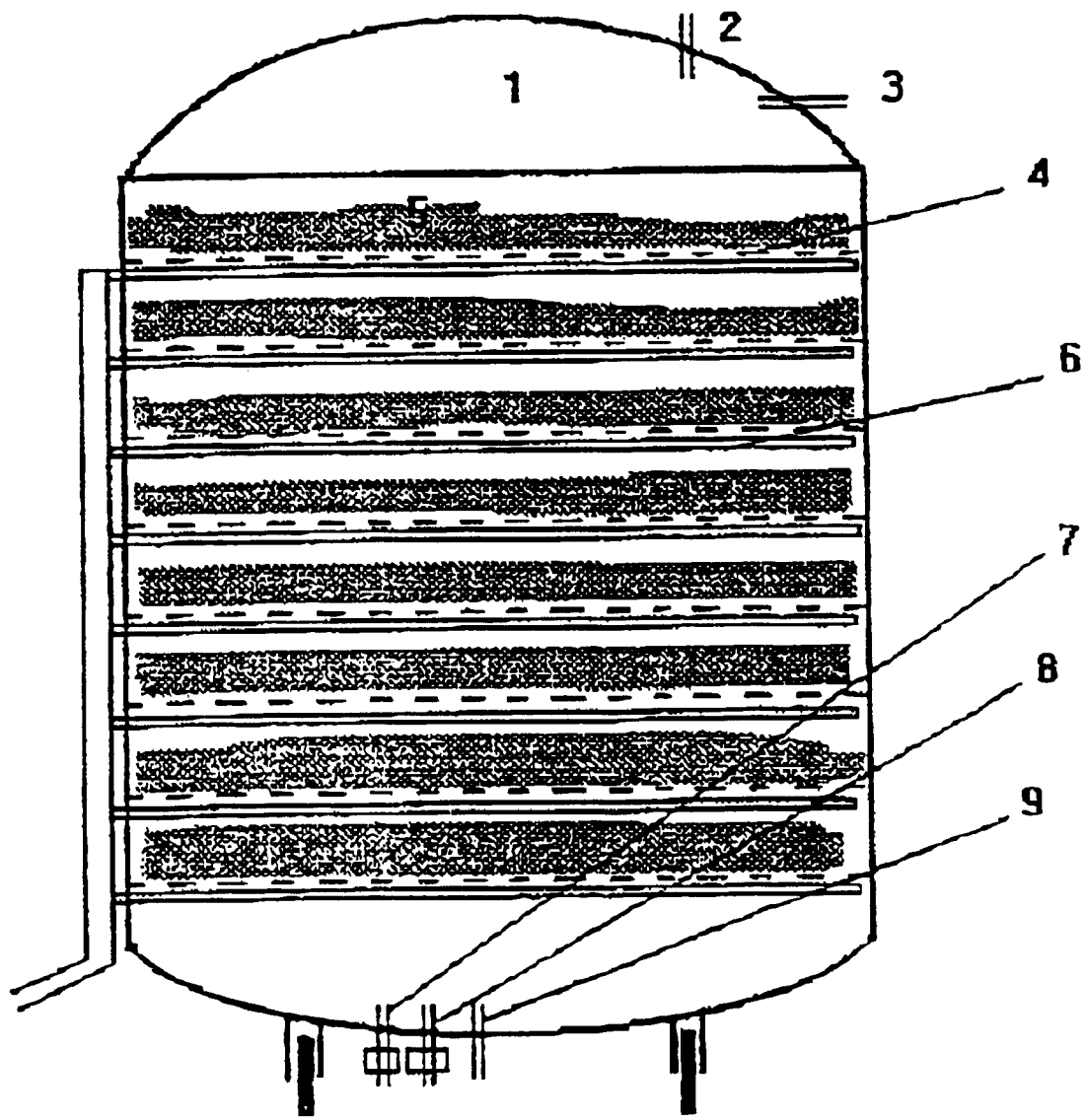
FIG. 1—principle drawing of the fermenter.

The task was solved according to the invention by a module fermenter, which has a capacity of at least 50 liters, preferably 500 liters to 1000 liters, but also allows higher capacities. The entire construction consists of a cylindrical or oval vessel (FIG. 1), that can be closed on top by a lid 1, which can be equipped, if necessary, with an air outlet 2 as well as with an orifice 3 for the inoculation of the fermenter.

The vessel, which is constructed as a shell impermeable to air and water, contains module bases 4 that are arranged in tiers and are permeable to air and vapor, which are for taking up of a cultivation substrate 5 for the microorganisms to be cultivated.

The cultivation substrate consists of different materials according to the respective nutrient requirement of the microorganism, which has to be cultivated. This material preferably has a granular structure in order to guarantee a sufficient permeability for air. It can, for example, consist of cereals, pellets of bran or other organic waste products, waste from the sugar production or granulates soaked with solution.

The number of tiers depends of the requirements of the cultivation of the microorganism to be cultivated as well as of the ease of servicing of the entire fermenter. Too many tiers could disturb the necessary supply of oxygen for the growth of the microorganisms (see below) in the upper layers of the cultivation substrate. Very many tiers deteriorate the ease of servicing of the fermenter, too. However, according to the invention, 20 or more tiers could be mounted in the fermenter.

The module bases are connected to the wall of the vessel in such a way, that neither air nor water can flow past them laterally. The distance between the module bases depends of the optimum layer thickness of the cultivation substrate, which is determined, on the other hand, by the requirements of the microorganism to be cultivated.

Figure 2:
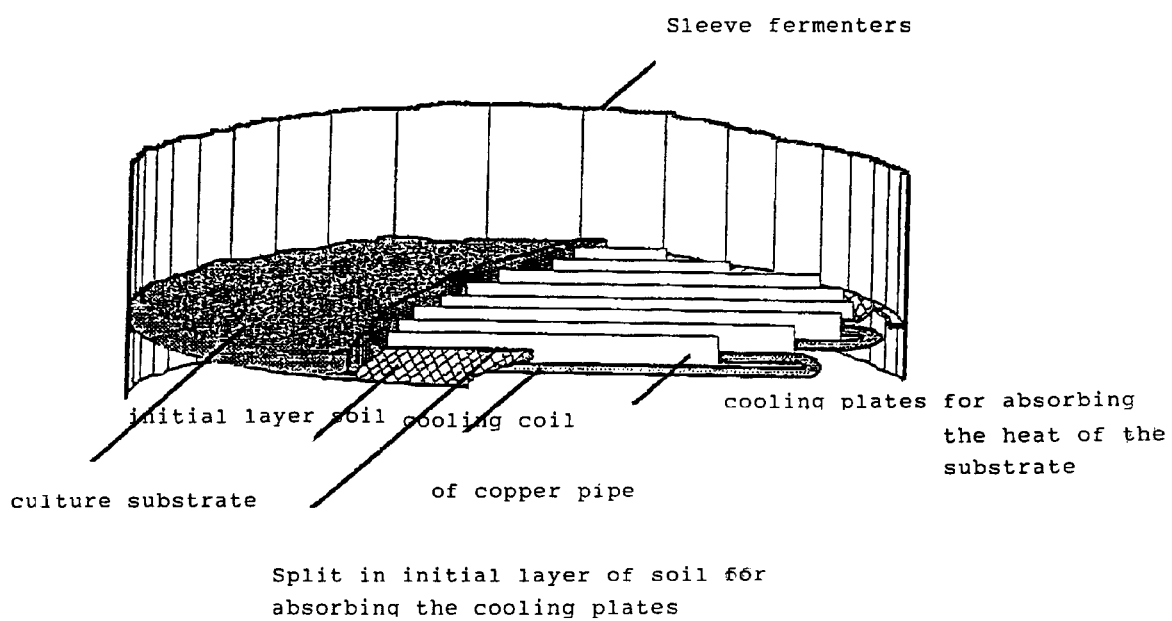
FIG. 2—cooling device of the fermenter with thermally conducting plates.

There are cooling devices 6 located below the module bases, which can be designed either as cooling coils or as cooling plates. They allow the evacuation of the heat of the reaction from the cultivation substrate. In a preferred variation, metal plates with a high thermal conductivity can reach into the cultivation substrate through the particular module base from each cooling device (FIG. 2). This makes the evacuation of the heat of the reaction easier. After completion of the fermentation process, the cooling device is pulled out together with the cooling plates in downwards direction from the module base for a removal of the cultivation substrate. Afterwards, it is possible to take out the cultivation substrate with the grown microorganisms, without an interference of the cooling plates.

It is also possible to mount the cooling devices in a certain distance above the module bases. In this case, they should be installed in such a manner, that they run in the middle of the layer of the cultivation substrate. The installation of the cooling devices within the substrate layers (parallel to the module bases) is especially to be included in the case when very much heat of reaction is produced in the process of fermentation.

The base of the fermenter contains an air-inlet 7, where sterile, moistened air is blown into the fermenter. The air circulates through all layers of substrate and leaves the fermenter through the air-outlet 2 mounted on the lid.

The interstices located between the modules, which also house cooling devices, guarantee an even distribution of the air in the entire fermenter. If no moistened air is available for the aeration of the fermenter, the air can also be moistened within the fermenter. This is realized by not filling up at least the lowest module base with a cultivation substrate, but with a granular material, which can absorb water, which is circulated first with the blown-in air before the air penetrates further into the fermenter. This moistens the air. If a large amount of water is required for the microorganism in development, several of such modules for moistening of the air can be installed with certain distances in the fermenter. The amount of air to be blown in depends of the oxygen requirement of the microorganism to be cultivated. It can vary between 1 and 100 liters per hour per liter of cultivation substrate.

The fermenter is filled with sterile water up to uppermost layer of cultivation substrate for the inoculation of the cultivation substrate with the microorganism to be cultivated after a sterilization of its content. A water inlet 8 is mounted for that reason, which has a sterile filter inserted. However, the water inlet can also be installed in a different place of the fermenter (e.g. on the lid). After the filling up, the inoculum is inserted through an orifice 3 in the lid, which is intended for this. Such orifices 3 for the inoculation of the fermenter can also be mounted between the single module bases especially if there are very many modules. In the first case the distribution of the inoculum in the fermenter is realized exclusively by letting out the water through an orifice 9 in the bottom of the fermenter, which is designed for this purpose.

The inoculum (suspension of micro-organisms) flows through all layers of cultivation substrate in this kind and remains in a sufficient amount with the adherent water on them. If there are to many layers, which have to be circulated, an effect of dilution can occur in dependence of the constitution of the cultivation substrate. This means that the microorganisms will be filtered through the cultivation substrate through which it has to circulate. Thus their concentration in the water decreases the lower they are. In order to prevent this, orifices for the insertion of the inoculum into the fermenter can also be mounted between the module bases in another variation. Inoculum can already inserted by their usage during the filling of the fermenter with water, which is distributed then with the water flow, which is directed upwards as well with the water flow, which is directed downwards.

The inoculum, which is used for the inoculation of the fermenter, consists of a highly concentrated suspension of small germinable units (preferably of spores, conidiospores or bacterial germs) of the microorganisms to be cultivated.

Under the condition of an even and sufficient inoculation of the inoculation vessel, the course of the cultivation (duration of the cultivation and yield of the product) as well as the quality of the cultivation product (e.g. fungal spores) mainly depends of the parameters of the cultivation care. It consists primarily in letting in moistened air and control of the temperature. The air volume flow has to be adjusted to the capacity of the air sterile filter. The control of the temperature in the fermenter is secured by the use of the cooling device, which is installed in the fermenter. The cooling capacity has to be designed in such a way, that it is possible to evacuate all the heat of reaction from the cultivation substrate and maintain an optimum temperature for the cultivation of the microorganism. The necessary cooling capacity also depends of the layer thickness and thus of the volume of the cultivation substrate. The more cultivation substrate is available for the growth of the microorganisms, the more heat of reaction is produced. That is why both parameters have to be optimized. Target is a development of the micro-organisms, that is as quick as possible, as well as a high yield of product, where the products can be depending on the aim of the fermentation, fungal spores, bacterial cells, enzymes, antibiotics, coloring substances and other substances.

Two design variations of the fermenter according to the invention are provided.

Figure 3:
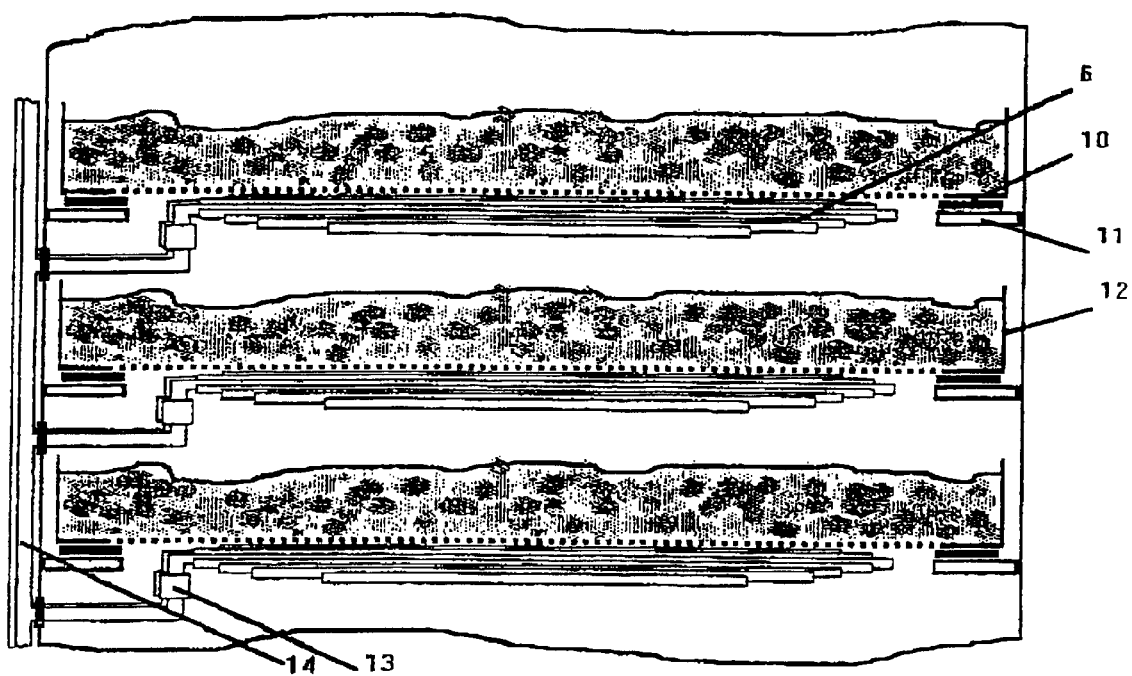
FIG. 3—selection of a fermenter consisting of a patent cylinder.

Variation 1. (FIG. 3)

The fermenter consists of a patent cylinder or a prism, which are tightly closed on the bottom. The cylinder (usually a circular cylinder) or the prism can have a diameter of 1 m and more. Its height is limited by the technical ease of servicing as well as by the possibility of maintaining optimum conditions for the microorganisms, which have to be calculated. It is possible to realize heights of 2 m and more.

The module bases 4 filled with cultivation substrate 5 are inserted from above in this cylinder or the prism. Rings, or in case of the use of a prismatic housing, devices of a different shape 11, are mounted in the interior of the container for the support of the module bases. Every ring or differently shaped support device is equipped with a heat resistant seal 10, e.g. of silicone, where the module bases are put on with their outer edges, which provides a seal between the module base and the vessel wall, that is impermeable for air and water. It is possible to take out the rings or differently shaped support devices from the housing. The cooling unit 6 below the module base, which can consist e.g. of a cooling coil made of copper, is connected by a quick coupling 13 with the pipes 14 to the inlet and outlet of the cooling liquid, which are located outside of the fermenter. Every module base is provided with an edge 12, whose height is adjusted according to layer thickness of the cultivation substrate. This avoids that the cultivation substrate falls into the fermenter vessel and its pollution.

The fermenter is tightly closed on top with the lid 1. It is designed as a pressure vessel and can be sterilized because of this by the entrainment of hot vapor, which is under pressure. Therefore, it is not necessary to use an autoclave.

Figure 4:
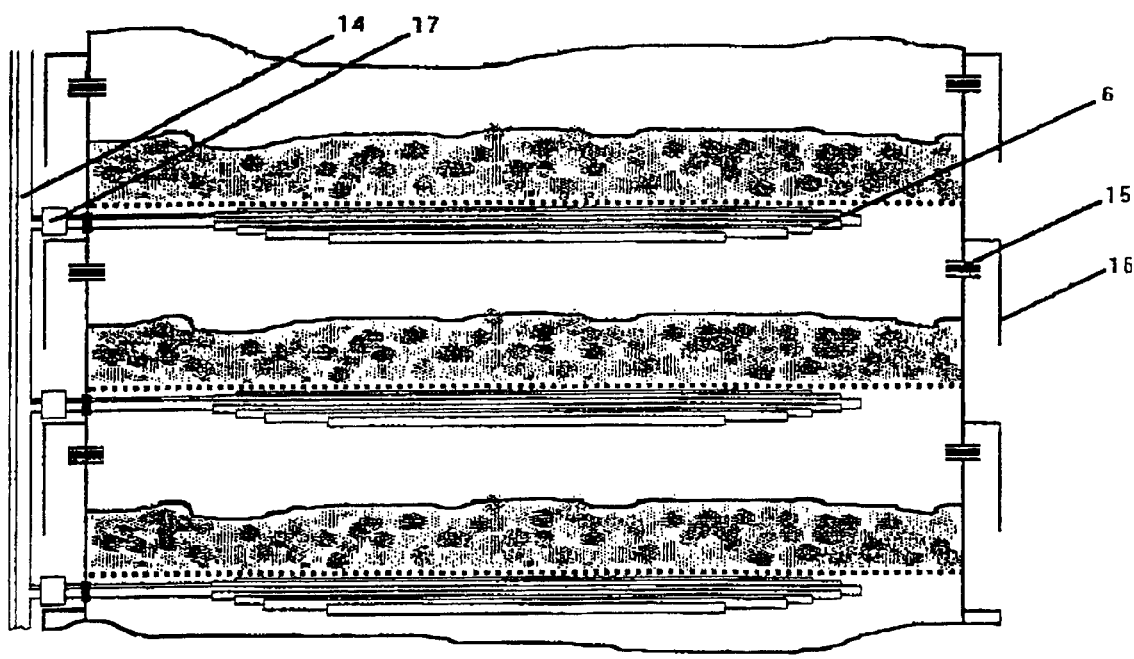
FIG. 4—section of an assembled fermenter.

Variation 2. (FIG. 4)

The fermenter consists of several cylinders or prisms always of little height (preferably about 7–30 cm), that can have a circular, oval, rectangular or another angular base. A bottom permeable for air and water is in each case mounted in all the single cylinders or prisms. The cooling device is located below the bottom, and on the bottom is the substrate for the cultivation of the microorganisms. The cylinders or prisms are used as modules 4 for the composite fermenter. They are arranged on top of each other and sealed from each other by heat resistant seals 15, which are located on the edges. The first module lies flush below against the fermenter bottom, and the last module is closed on top by the fermenter lid. Thus the fermenter can be assembled preferably of 10 or more modules. As it is difficult to design such a composite fermenter as a pressure vessel, the sterilization of the fermenter and of the cultivation substrate within is realized in an autoclave. Thus the height of the fermenter is in the first place dependant of the capacity of the autoclave that is available. As a result, it will have to be limited in most cases to a volume of 500–1000 liters. During the autoclaving the fermenter is still open, that means, the single modules are slightly (approximately 5 mm) lifted from each other. This allows a good feeding of the hot vapor into the interior of the fermenter, which causes the sterilization. The fermenter is closed tightly after the autoclaving. Every module is equipped with an exterior ring 16, which is designed for overlapping the existing gap between the modules, when the fermenter is opened, in order to avoid a contamination of the fermenter with nucleus of crystallization after the autoclaving and before the closing, i.e. when the fermenter is taken out from the autoclave.

After the fermenter is closed the cooling devices 6, which are located below the module bases are connected by a coupling 17 with the pipes 14, which are used for the supply and drain of the cooling liquid.

In a preferred design variation a granular cultivation substrate, where microorganisms shall develop, consists of a 5–6 cm thick layer. Up to 10 of such layers are arranged on top of each other. The granular cultivation substrate, which is arranged in layers, is each time put on a perforated bottom and thus, on a bottom permeable for air, below which is a cooling coil (wound copper pipe), which can be used for evacuating the heat, that is generated in the substrate. The supply of the sterile filtered air comes from below. The air is forced to circulate all the modules (layers of cultivation substrate) evenly, because of the lateral hermetic sealing, before it can leave the fermenter again on the top end. On the lowest module base is a water-saturated layer, preferably SERAMIS granulate, through which the air is conducted moistening it in such a way.

The sterilization of the fermenter together with the already inserted cultivation substrate is realized preferably by vapor, that is heated up to 121° C., preferably in autoclaves, whereas the single modules are slightly lifted from each other during the autoclaving process, thus allowing the hot vapor to intrude into the modules.

Further data:
  volume: 500 liters
amount cultivation substrate: 250 liters
air volume flow: 1500 liters per hour
power of the cooling system: 2.5 kW Differently to the types used so far (swing solid state fermenter or rotary fermenter), where a constant overturn of the cultivation substrate has to be realized for a heat removal, aeration and water supply, it is no longer necessary to move the substrate with the use of the method according to the invention. The storage of the cultivation substrate in tiers of layers, which are sheathed as a whole by a closed shell provides the following advantages:

1. The own weight of the cultivation substrate does not lead to a densification and as a result of that to a reduction of permeability for air of it.

2. The installation of a cooling device below the single modules allows an easier evacuation of the generated heat.

3. Due to a relatively small thickness of the modules as well as the spaces between the modules an even aeration of the substrate layers is guaranteed.

4. As the aeration of the substrate is only used for supplying oxygen as well as for evacuating generated gases and not for the cooling of the substrate, it is possible to work with a very low air volume flow, which does no longer lead to an exsiccation of the substrate a the air is moistened.

5. As it is no longer necessary to move the substrate, mechanical destruction of fungal structures (sporangium, fructovegetative body etc.) can be ruled out.

Example 1

Mass Cultivation of *beauveria brongniartii* for the Purpose of Yielding Fungal Conidii The fermenter used for the cultivation of *beauveria brogniartii* has a capacity of about 50 liters. It has the shape of a cylinder with a diameter of 30 cm and a height of 70 cm. The outer shell of the fermenter is made of heat resistant glass. Eight modules were mounted in the fermenter, whose bottoms consist of a stainless screen with a screen aperture of 3 mm. The distance between the module bases was 8 cm. The lower bottom was filled with a 6 cm thick layer of SERAMIS granulate. The 7 modules arranged above contained crushed barleycorns as cultivation substrate. The layer thickness of the cultivation substrate was approximately 6 cm. In total 30 liters of cultivation substrate were used.

The fermenter was sterilized by an autoclave. For this purpose, the content of the fermenter was heated by hot vapor to 121° C. for a period of half an hour. The lid of the fermenter was slightly opened during the process of autoclaving in order to allow the permeation of the vapor into the interior of the fermenter. It was closed immediately after autoclaving.

The fermenter was filled over the uppermost layer of the cultivation substrates with sterile water for the inoculation. A 500 $cm^2$ capsule of the type S+S-EXELON PES 20/5 HC (Schleicher und Schuell, Dassel) was used for this. After that, the inoculum was inserted through an orifice in the lid designed for this purpose. The inoculation of the fermenter occurred under a laminar box. The used inoculum was a 100 ml of a conidium suspension with $1\times10^9$ conidii per ml. After the insertion of the inoculum over the upper layer of the cultivation substrate, the water was drained through a valve in the fermenter bottom. All the layers of substrate were contaminated evenly with fungal conidii.

After the inoculation of the fermenter, it was incubated in a room with a temperature of 20° C. A connection to the air supply as well as to the cooling system followed. The air volume flow during the entire fermentation process was 150 liters per hour. Water was used as cooling liquid with a supply temperature of 17° C. The control of the cooling was adjusted in such a way, that the cooling liquid was pumped through the cooling coil, if 22° C. were exceeded in the cultivation substrate, until it had cooled down again to 20° C. In this way, an average substrate temperature of about 21° C. could be maintained during the entire time of the cultivation.

The goal of the cultivation was a yield of as many fungal conidii as possible. The glass sheathe of the fermenter allowed a very good observation of the course of the cultivation. The entire cultivation substrate was covered by a white mycelium after about 10 days. This mycelium changed its appearance form the $13^{th}$ day on because of the build-up of conidii and of conidiophores. It changed to a powdered structure. The fermenter had a clear decrease in metabolism activity after about 19 days. The evolution of heat decreased, which clearly reduced the cooling frequency. The cultivation substrate was taken out 21days after the inoculation of the fermenter and the conidii were extracted by a special filtration technique from the cultivation substrate, which then was completely grown with *beauveria brogniartii*. A total amount of $3.3\times10^{13}$ conidii could be extracted with the module fermenter.

LIST OF REFERENCE SIGNS

1 lid
2 air-outlet
3 fermenter
4 module base permeable for air
5 cultivation substrate
6 cooling device
7 air-inlet
8 water supply
9 water discharge
10 heat resistant seal
11 support device for the module base
12 edge of the module base
13 quick coupling
14 pipe for the inflow and outflow of the cooling liquid
15 heat resistant seal
16 exterior ring
17 coupling

What is claimed is:

1. A solid state fermenter comprising at least two module bases that are permeable to air and water and that are arranged one above the other, wherein the module bases contact a wall of the vessel thereby preventing the lateral passage of water or air, the fermenter further comprising on each of the module bases a cultivation substrate suitable for cultivating microorganisms, and a cooling unit mounted below each module base, and a lid.

2. The fermenter according to claim 1, wherein the fermenter comprises a patent cylindrical, oval, rectangular or differently angular container with at least one orifice (3) for the inoculum.

3. The fermenter according to claim 1, wherein metal plates with a high thermal conductivity that protrude from the cooling device, through the respective module base into the cultivation substrate.

4. The fermenter according to claim 1, wherein the existence of a water supply (8) on the container, of an air-inlet (7) on the bottom of the fermenter as well as of a water discharge (9) and the existence of an orifice on the lid (1) for the outlet of air (2), module bases (4) filled with cultivation substrate (5), that were placed one after the other, for which rings or devices of different shape (11) are mounted in the interior of the container for the support of the module bases (4), that are equipped with a heat resistant seal (10) and module bases having an edge (12), whose height depends of the thickness of the layer of the cultivation substrate as well as cooling devices (6) that are connected via a quick coupling (13) with pipes (14) for discharge and supply of the cooling liquid, which are outside of the fermenter.

5. The fermenter according to claim 4, wherein the mounting place of the water supply (8) is in the bottom or in the lid of the fermenter.

6. The fermenter according to claim 1 wherein the lid comprises an orifice for the inoculum and if necessary additional orifices for the inoculation arranged between the single module bases.

7. The fermenter according to one of the claim 1, wherein the fermenter containing several cylindrical, oval or prismatic containers, that serve as modules, and that are arranged on top of each other in such a way that the first container is supported below on the fermenter bottom and that the last one is closed with a lid (1), and that the containers are sealed from each other with heat resistant seals (15) and are equipped with an exterior ring (16), the existence of a base (4) that is permeable for air and water in each of the containers, where the cultivation substrate (5) is located and below which cooling device (6) is, which is connected by means of a coupling (17) with the inflow and outflow pipes (14) for the cooling liquid, that are outside of the fermenter.

8. The fermenter according to claim 1, wherein the cultivation substrate being porous granulates with an added nutrient solution or being natural granular materials.

9. The fermenter according to claim 8, wherein cereals, pellets of bran or waste from the sugar production are natural granular materials.

10. The fermenter according to claim 1, wherein the existence of a moistening layer, which is at least on the lowest module base.

11. The fermenter according to claim 10, wherein the moistening layer being a granular material capable of absorbing water with an extremely high pore volume.

12. A procedure for solid state fermentation with a device according to claim 1, wherein a cultivation substrate, which is in several module bases in the fermenter, evenly inoculated, completely flowed through by a relatively low air volume flow and for which the optimum temperature is adjusted by means of the cooling system for the respective cultivation procedure.

13. The procedure according to claim 12, wherein a realization of the inoculation with the micro-organism, which is to be multiplied by filling up water in the fermenters, to which the germs are added in a sufficient amount and in a manner, that all the layers are evenly and flowed through during the filling as well as during the discharging.

14. The procedure according to claim 12, wherein the cooling capacity is regulated in dependence of the volume of the cultivation substrate in such a manner that the whole heat of reaction is evacuated from cultivation substrate.

* * * * *